United States Patent [19]

Fisher et al.

[11] 4,174,352

[45] Nov. 13, 1979

[54] PROCESS FOR AQUEOUS CHROMATE ION OXIDATION OF ALLYLIC HALIDES AND HALOMETHYLATED AROMATICS TO ALLYLIC AND AROMATIC ALDEHYDES

[75] Inventors: Thomas H. Fisher; William Dowd, both of Midland, Mich.

[73] Assignee: The Dow Chemical Company, Midland, Mich.

[21] Appl. No.: 903,425

[22] Filed: May 8, 1978

[51] Int. Cl.$^2$ .............................................. C07C 45/00
[52] U.S. Cl. .............................. 260/599; 260/601 R; 562/459; 562/577; 260/600 R; 260/602
[58] Field of Search ............... 260/599, 601 R, 600 R, 260/602; 562/459, 577

[56] References Cited

U.S. PATENT DOCUMENTS 3,992,432  11/1976  Napier et al. ................ 260/604 HF
4,061,664  12/1977  Wood ................................ 560/124

OTHER PUBLICATIONS

Cardillo et al., Jour. Chem. Soc. (London) Chem. Comm. (1976), p. 190.
Kulka, Amer. Perfumer Aromatics, vol. 69, (Feb. 1957), 31-33.
Kulka, Amer. Perfumer Aromatics, vol. 70 (Nov. 1957), 37-39.

*Primary Examiner*—Bernard Helfin
*Attorney, Agent, or Firm*—G. R. Plotecher

[57] ABSTRACT

A process for preparing an allylic or an aromatic aldehyde, such as acrolein or benzaldehyde, the process comprising contacting in a basic, liquid, biphasic mixture and at reactive conditions an allylic halide or a halomethylated aromatic, such as allyl or benzyl chloride, with a divalent chromate ion, is improved by contacting the allylic halide or halomethylated aromatic with the divalent chromate ion in the presence of a catalytic amount of a quaternary ammonium and/or phosphonium salt, such as tetra-n-butylammonium chloride. The improved process is faster, cleaner and more complete than the process of the prior art.

5 Claims, No Drawings

PROCESS FOR AQUEOUS CHROMATE ION OXIDATION OF ALLYLIC HALIDES AND HALOMETHYLATED AROMATICS TO ALLYLIC AND AROMATIC ALDEHYDES

BACKGROUND OF THE INVENTION

1. Field of the Invention

This invention relates to the divalent chromate ion oxidation of an allylic halide or a halomethylated aromatic to an allylic or aromatic aldehyde.

2. Description of the Prior Art

Kulka, Am. Perfumer Aromat., 69, 31 (February, 1957) and 70, 31 (November, 1957), teaches the oxidation of p-methylbenzyl chloride with aqueous sodium dichromate in the presence of sodium bicarbonate. After 20 hours of reflux, p-tolualdehyde in 90 percent yield was recovered by steam distillation. The use of a catalyst is not reported.

Cardillo et al., J.C.S. Chem. Comm., 190 (1976) and Tetrahedron Let., 44, 3985-6 (1976), teach the reaction between an alkyl, allylic or benzylic halide and potassium dichromate ($K_2CrO_4$) in hexamethylphosphoramide (HMPA) in the presence of molar quantities of a crown ether to obtain moderate to good yields of aldehydes and ketones. Due to the general insolubility of $K_2CrO_4$ in HMPA, Cardillo et al. supported $K_2CrO_4$ on an insoluble polymer matrix.

SUMMARY OF THE INVENTION

According to this invention, a process for preparing an aldehyde of the formula $$A{-}(CHO)_n \qquad (I)$$

wherein A is an allylic, aryl or an inertly-substituted allylic or aryl radical and n is an integer of at least 1, the process comprising contacting in a basic, liquid, biphasic mixture and at reactive conditions a compound of the formula $$A{-}(CH_2X)_n \qquad (II)$$

wherein X is chloride or bromide, preferably chloride, and A and n are as previously defined, with divalent chromate ion, is improved by contacting II with the chromate ion in the presence of a catalytic amount of a quaternary ammonium and/or phosphonium salt. The improved process is characterized by short reaction times, high yields and good selectivity.

DETAILED DESCRIPTION OF THE INVENTION

The compounds of II are allylic halides, halomethylated aromatics and inertly-substituted allylic halides and halomethylated aromatics. As used herein, "halide", "halo-" and like terms refer to chloride and bromide but not fluoride, iodide or astatine, "allylic" refers to compounds containing the moiety

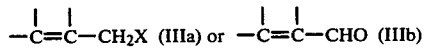

and "inertly-substituted" means that the allylic or aromatic compound or radical can bear 1 or more substituents that are essentially nonreactive toward the process reagents or products at the process conditions. Typical inert substituents include: alkyl and alkoxy radicals of 1 to about 18 carbon atoms, halogen (other than the halogen in the halomethyl ($-CH_2X$) moiety), carboxyl, nitro, aryl, aryloxy, hydroxyl, ethylenic unsaturation, etc. Where A in II is a phenyl radical, these inert substituents can be ortho, meta and/or para to the halomethyl moiety.

A in II can be any suitable allylic, aryl or inertly-substituted allylic or aryl radical. Representative radicals include: allylic and inertly-substituted allylic radicals of the formula

wherein R and each R' are individually hydrogen, an aliphatic, alicyclic, aryl or an inertly-substituted aliphatic, alicyclic or aryl radical and the open valence is the bond which links the radical to the halomethyl moiety; aryl radicals, such as phenyl, naphthyl, anthracyl, phenanthracyl, etc.; and inertly-substituted aryl radicals, such as phenethyl, hydroxyphenyl, hydroxynaphthyl, phenoxyphenyl, biphenyl, triphenyl, methoxybiphenyl, etc. Preferably, A in II is either an allylic or inertly-substituted allylic radical where, in IV, R is hydrogen or methyl and each R' is individually hydrogen or an alkyl radical of 1 to about 8 carbon atoms, or phenyl or an inertly-substituted phenyl radical. Most preferably, A in II is phenyl and II is benzyl halide, especially benzyl chloride.

n Is the number of halomethyl moieties attached to A. The size of n is dependent upon A; the larger A is, generally, the larger n can be. n Is at least and preferably 1.

Any source of divalent chromate ion can be used in the practice of this invention. "Divalent chromate ion" here means an ion of the formula $$CrO_4^{=} \qquad (V)$$

wherein the chromium atom has a valence of plus 6. Representative of the many known sources of chromate ion include the alkali metal chromates, the alkaline earth metal chromates, silver chromate, lead chromate, etc. The alkali metal chromates and magnesium chromate are preferred to the other sources of chromate ion because of their greater solubility in water. For reasons of convenience and general availability, sodium dichromate is the preferred source of chromate ion.

The catalysts here used are quaternary ammonium and phosphonium salts (here termed collectively "onium" salts) and are known in the art as phase transfer catalysts. The salts are described by Starks and Napier in U.S. Pat. No. 3,992,432 and British Patent 1,227,144 and by Starks in the J. Amer. Chem. Soc., 93, 195 (1971). Suitable onium salts have a minimum solubility of at least about 1 weight percent in both the organic phase and the aqueous phase at 25° C. The ammonium salts are preferred over the phosphonium salts and benzyltrimethyl-, benzyltriethyl- and tetra-n-butyl ammonium chlorides and bromides are most preferred.

As a further illustration of the onium salts here used, suitable onium salts are represented by the formula $$R''R'''R^{IV}R^{V}Q^{\oplus}An^{\ominus} \qquad (VI)$$

wherein $Q^\oplus$ is a quaternized atom of nitrogen or phosphorus, $R''$-$R^V$ are hydrocarbyl groups, e.g., alkyl, aryl, aralkyl, cycloalkyl, etc., and $R''$ can join with $R'''$, or $R'''$ with $R^{IV}$, etc. to form a 5- or 6-membered heterocyclic compound having at least one quaternized nitrogen or phosphorus atom in the ring and they also contain one nonadjacent atom of oxygen or sulfur within the ring. Typically, $R''$—$R^V$ are hydrocarbyl groups of 1 to about 16 carbon atoms each, with a combined minimum total of about 10 carbon atoms. Preferred onium salts have from about 10 to about 30 carbon atoms.

The neutralizing anion portion of the salt, i.e., $An^\ominus$ in VI above, may be varied to convenience. Chloride and bromide are the preferred anions, but other representative anions include fluoride, iodide, tosylate, acetate, bisulfate, etc. The following compounds serve as a further illustration: tetraalkyl ammonium salts, such as tetra-n-butyl-, tri-n-butyl-methyl-, tetrahexyl-, trioctylmethyl-, hexadecyltriethyl- and tridecylmethyl ammonium chlorides, bromides, iodides, bisulfates, tosylates, etc.; aralkyl ammonium salts, such as tetrabenzyl-, benzyltrimethyl-, benzyltriethyl-, benzyltributyl- and phenethyltrimethyl ammonium chlorides, bromides, iodides, etc.; aryl ammonium salts, such as triphenylmethylammonium fluoride, chloride or bromide, N,N,N-trimethylanilinium chloride, N,N,N-triethylanilinium bromide, N,N-diethylanilinium bisulfate, trimethylnaphthylammonium chloride, p-methylphenyltrimethylammonium chloride or tosylate, etc.; 5- and 6-membered heterocyclic compounds containing at least 1 quaternary nitrogen atom in the ring, such as N,N-dibutylmorpholinium chloride, N-decylthiazolium chloride, etc.; and the corresponding phosphonium salts.

Stoichiometric amounts of divalent chromate ion and halomethyl moiety of II are used in the practice of this invention. Although an excess of either component can be used, such a practice is generally disfavored. Excess divalent chromate ion can cause some loss of product (aldehyde) by further oxidizing the product to a carboxylic acid, e.g., benzaldehyde to benzoic acid. Excess halomethyl moieties (equivalents) results in incomplete conversion of the halomethyl moiety to the corresponding aldehyde.

A catalytic amount of the onium salt is required in the practice of this invention. The concentration will vary with the reagents employed, however best results are generally achieved where the onium salt concentration is from about 1 mole percent to about 30 mole percent based upon the allylic halide or halomethylated aromatic (or halomethyl equivalents). Onium salt concentrations of about 2 mole percent to about 10 mole percent are preferred.

The reaction medium of this invention is a biphasic mixture of an aqueous phase and an organic phase. The aqueous phase contains the source of divalent chromate ion, the onium salt and typically an alkaline buffer. The organic phase contains the allylic halide or halomethylated aromatic. The reaction medium is typically agitated throughout the course of the oxidation.

Temperature and pressure are not critical to this invention as long as the biphasic mixture remains a liquid. A temperature of about 20° C. to about 100° C. is typically employed with a temperature of about 40° C. to about 70° C. preferentially employed. The oxidation can be conducted at reduced, atmospheric or superatmospheric pressure. Autogenous, usually atmospheric, pressure is preferred.

Although this process is usually conducted neat, it can be conducted in the presence of an inert, essentially water-immiscible organic solvent. Typical solvents include benzene, chlorobenzene, o-dichlorobenzene, hexane, methylene chloride, chloroform, carbon tetrachloride, and the like. Sufficient solvent to dissolve the allylic halide or halomethylated aromatic is used and preferably the amount of solvent used is equal in volume to the amount of aqueous medium employed.

The reaction medium of this invention is basic, i.e., has a pH value in excess of 7. Preferably, the reaction medium has a pH value between about 7 and 10 and this value can be obtained and maintained by the use of any suitable alkaline buffer. Representative buffers include sodium carbonate, potassium carbonate, etc. Sufficient alkaline buffer is used to maintain a pH value in excess of 7 throughout the process.

The following example is an illustrative embodiment of this invention. Unless otherwise indicated, all parts and percentages are by weight.

SPECIFIC EMBODIMENTS

EXAMPLE

A 250 ml 3-neck, round-bottom flask fitted with a magnetic stirrer and reflux condenser was charged with benzyl chloride (37 g, 0.3 mole) and deionized water (150 ml). The two immiscible liquid layers were stirred rapidly and charged with sodium carbonate (6 g, 0.057 mole) and Adogen® 464 (10 g, 0.02 mole, 7 mole percent), a quaternary ammonium salt having three $C_8$–$C_{10}$ alkyl groups and one methyl group manufactured by Archer Daniels Midland Co. Sodium dichromate of the formula $Na_2Cr_2O_7 \cdot 2H_2O$ (34.1 g, 0.14 mole) was then added slowly, and after complete addition of the sodium dichromate, the reaction mixture was heated to reflux. After 2 hours of reaction, gas chromatographic analysis indicated that better than 90 percent of the benzyl chloride had been converted to benzaldehyde.

CONTROL

The above example was repeated except that no catalyst was employed, i.e., Adogen® 464 was not used. After 20 hours of reflux, less than 90 percent of the benzyl chloride had been converted to benzaldehyde.

In both the example and control, the sodium dichromate was converted to the divalent chromate ion according to the following reaction:

$$Cr_2O_7^= + CO_3 \rightarrow CrO_4^= + CO_2 \qquad \text{(VII)}$$

The divalent chromate ion is converted by the oxidation of the halomethyl moiety to a chromate ion of plus 3 valence which can, if desired, be reoxidized to a chromate ion of a plus 6 valence. This provides recycleability and thus good ecology and good economics. Carbon dioxide is released throughout the process.

A comparison of the results between the example and the control demonstrates the improved characteristics of this invention. Not only was the process of the example completed in a shorter time, but also generated a better yield of benzaldehyde.

Although this invention has been described in detail by the preceding example, such detail is for the purpose of illustration only and is not to be construed as a limitation upon the invention. Many variations can be had upon the preceding example without departing from the spirit and scope of the appended claims.

What is claimed is:

1. An improved process for preparing an aldehyde of the formula $$A\text{---}(CHO)_n \quad (I)$$

wherein A is an allylic, aryl or an inertly-substituted allylic or aryl radical and n is an integer of at least 1, the process comprising contacting in a basic, liquid, biphasic mixture and at reactive conditions a compound of the formula $$A\text{---}(CH_2X)_n \quad (II)$$

wherein X is chloride, bromide or iodide and A and n are as previously defined, with divalent chromate ion, the improvement comprising contacting II with the chromate ion in the presence of a catalytic amount of a quaternary ammonium and/or phosphonium salt.

2. The process of claim 1 where the quaternary ammonium and/or phosphonium salt is present in an amount of from about 1 to about 30 mole percent based on the moles of II.

3. The process of claim 1 whre the quaternary ammonium and/or phosphonium salt is present in an amount of from about 2 to about 10 mole percent based on the moles of II.

4. The process of claim 1, 2 or 3 where the quaternary ammonium and/or phosphonium salt is of the formula $$R''R'''R^{IV}R^{V}Q^{\oplus}An^{\ominus} \quad (III)$$

where $Q^{\oplus}$ is a quaternized atom of nitrogen or phosphorus and $R''$-$R^V$ are hydrocarbyl groups of 1 to about 16 carbon atoms each with a combined minimum total of about 10 carbon atoms.

5. The process of claim 4 where the quaternary ammonium and/or phosphonium salt is benzyltrimethyl-, benzyltriethyl- or tetra-n-butylammonium chloride or bromide.